US011207689B2

(12) United States Patent
Cho et al.

(10) Patent No.: US 11,207,689 B2
(45) Date of Patent: Dec. 28, 2021

(54) CARTRIDGE FOR EXTRACTING NUCLEIC ACID

(71) Applicant: SD BIOSENSOR, INC., Suwon-si (KR)

(72) Inventors: Young Shik Cho, Yongin-si (KR); Hyo Guen Lee, Suwon-si (KR); Hae Joon Park, Seongnam-si (KR); Sun Young Lee, Suwon-si (KR); Kwan Hun Lim, Suwon-si (KR); In Ae Kim, Gwangmyeong-si (KR); Jae Young Kim, Suwon-si (KR); Hyo Lim Park, Suwon-si (KR); Dong Hun Kim, Suwon-si (KR)

(73) Assignee: SD BIOSENSOR, INC., Suwon-si (KR)

( * ) Notice: Subject to any disclaimer, the term of this patent is extended or adjusted under 35 U.S.C. 154(b) by 0 days.

(21) Appl. No.: 16/956,584

(22) PCT Filed: Dec. 27, 2018

(86) PCT No.: PCT/KR2018/016775
§ 371 (c)(1),
(2) Date: Jun. 20, 2020

(87) PCT Pub. No.: WO2019/132546
PCT Pub. Date: Jul. 4, 2019

(65) Prior Publication Data
US 2021/0283595 A1     Sep. 16, 2021

(30) Foreign Application Priority Data

Dec. 28, 2017 (KR) .......................... 10-2017-0182628

(51) Int. Cl.
*B01L 3/00* (2006.01)
*C12N 15/10* (2006.01)

(52) U.S. Cl.
CPC .......... *B01L 3/508* (2013.01); *C12N 15/1003* (2013.01); *B01L 2200/06* (2013.01);
(Continued)

(58) Field of Classification Search
CPC ............. B01L 3/508; B01L 2300/0681; B01L 2200/06; B01L 2300/0861; C12N 15/1003
See application file for complete search history.

(56) References Cited

U.S. PATENT DOCUMENTS

2003/0162304 A1* 8/2003 Dority ............... B01L 3/502738
436/180

FOREIGN PATENT DOCUMENTS

JP     2004-208654        7/2004
JP     2004208654 A  *   7/2004
(Continued)

OTHER PUBLICATIONS

European Search Report for EP18894723.8 dated Aug. 20, 2021.

*Primary Examiner* — Jennifer Wecker
*Assistant Examiner* — Jonathan Bortoli

(57) ABSTRACT

There is provided a cartridge for nucleic acid extraction comprising: a first body having a plurality of chambers in which ports are formed at the bottom; a second body coupled to a lower region of the first body; and a piston disposed rotatably in the centers of the first body and the second body and having a port formed at the bottom thereof; and characterized in that the cartridge comprises a plurality of flow paths formed on the upper region of the second body, one end overlapping the port of the piston and the other end overlapping the port of the first body.

10 Claims, 9 Drawing Sheets

(52) U.S. Cl.
CPC ............... *B01L 2300/0681* (2013.01); *B01L 2300/0861* (2013.01)

(56) References Cited

FOREIGN PATENT DOCUMENTS

| | | |
|---|---|---|
| JP | 2005-518532 | 6/2005 |
| KR | 2014-0046941 | 4/2014 |
| KR | 2016-0035945 | 4/2016 |
| WO | WO2016/117726 | 7/2016 |

* cited by examiner

CARTRIDGE FOR EXTRACTING NUCLEIC ACID

TECHNICAL FIELD

The present invention is generally related to a cartridge for nucleic acid extraction, more specifically to cartridge that can separate and purify nucleic acids from samples to amplify nucleic acids.

BACKGROUND ART

In modern times, it has become possible to interpret the cause of disease at the gene level with the development of biotechnology. As a result, the demand for manipulation and biochemical analysis of biological specimens to treat or prevent human diseases is increasing.

Also, in addition to the diagnosis of disease, the technology for extracting and analyzing nucleic acids from samples containing cells or biological specimens is required in various fields such as new drug development, preliminary examination of virus or bacterial infection, and forensic science.

Traditional nucleic acid extractors require each device for each processing process (concentration, purification) and require a long time to move to another device after one processing process is completed.

To address the traditional problem of low detection efficiency with such a long process, U.S. issued patents U.S. Pat. No. 6,374,684 created multiple bifurcated flows (34,38, 42,44) on the piston head, allowing the piston head to rotate and directly inhale reagents in the chamber to mix them in the inner space of the piston (see FIG. 1). In other words, a single cartridge was used to treat multiple reagents at once.

However, according to U.S. Pat. No. 6,374,684 the production cost of the piston may increase because multiple divergent flow paths must be generated inside the piston head, and even small errors in the manufacturing process may have a severe effect on device performance.

DISCLOSURE

Technical Problem

The purpose of this invention is to provide cartridges for extracting nucleic acids in a simpler and more efficient structure.

Technical Solution

In order to achieve the above object, a cartridge for nucleic acid extraction according to an embodiment of the present invention comprises cartridge for nucleic acid extraction comprising: a first body having a plurality of chambers in which ports are formed at the bottom; a second body coupled to a lower region of the first body; and a piston disposed rotatably in the centers of the first body and the second body and having a port formed at the bottom thereof; wherein the cartridge comprises a plurality of flow paths formed on the upper region of the second body, one end overlapping the port of the piston and the other end overlapping the port of the first body.

According to an embodiment of the present invention, the port of the piston comprises at least two ports formed at a certain angle apart, and at least one of the ports is provided with a filter mounting region.

According to an embodiment of the present invention, the two ports are formed 22.5 degrees apart on the same circumference.

According to an embodiment of the present invention, it further comprises a pad disposed between the first body and the second body and formed to cover the flow path.

According to an embodiment of the present invention, the pad includes a plurality of holes overlapping the ends of the flow path.

According to an embodiment of the present invention, a recessing region to which the pad is combined is formed on the upper surface of the second body, and the pad is made of a rubber material and is formed to be engaged with and fixed to the recessing region.

According to an embodiment of the present invention, it further comprises a nucleic acid amplification module which is mounted on the first body or the second body, having an internal flow path where one end overlaps with at least one of the plurality of flow paths.

According to an embodiment of the present invention, the inner flow path is connected to a first flow path and a second flow path, respectively, and when the first flow path overlaps the port of the piston, the second flow path is formed to overlap the vacuum removal groove of the piston.

According to an embodiment of the present invention, the vacuum removal groove and the port of the piston are disposed on different circumferences.

According to one embodiment of the invention, the ports of the first body are formed on the same circumference.

Effects of the Invention

According to the cartridge for nucleic acid extraction according to an embodiment of the present invention, the internal flow path of the piston can be simplified to improve cartridge design and production efficiency.

In addition, according to the cartridge for nucleic acid extraction according to an embodiment of the present invention, it is possible to improve the mixing efficiency of the sample and the reagent by expanding the interior space of the piston in which the sample and the reagent are mixed.

In addition, according to the cartridge for nucleic acid extraction according to an embodiment of the present invention, a flow path through which a sample and a reagent are moved is formed on an upper surface of a lower body of the cartridge, thereby facilitating flow path fabrication and checking the condition of the flow path.

In addition, according to an embodiment of the present invention, a rubber pad is disposed between the upper body and the lower body of the cartridge to prevent the liquid from leaking while using the cartridge.

MODE FOR INVENTION

Figure 1:
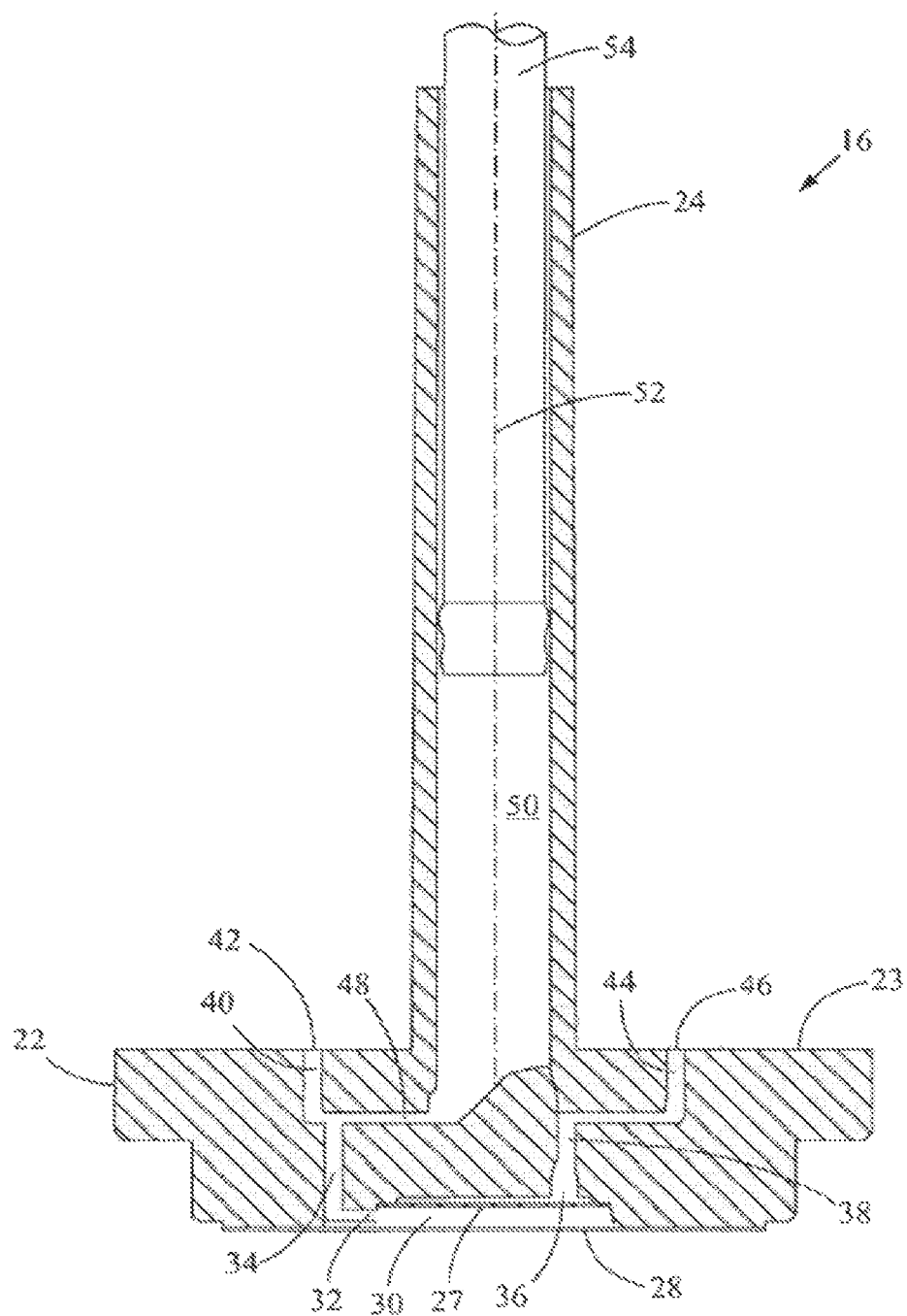
FIG. 1 is a conceptual diagram showing the piston of a cartridge applied to the prior art.

Hereinafter, the present invention will be described in more detail with reference to the drawings. In this specification, the same or similar reference numerals are assigned to the same or similar configurations in different embodiments, and the description is replaced with the first description. As used herein, a singular expression includes a plural expression unless the context clearly indicates otherwise. In addition, the suffixes "module" and "region" for components used in the following description are given or mixed only considering the ease of writing the specification, and do not have meanings or roles that are distinguished from each other.

Figure 2:
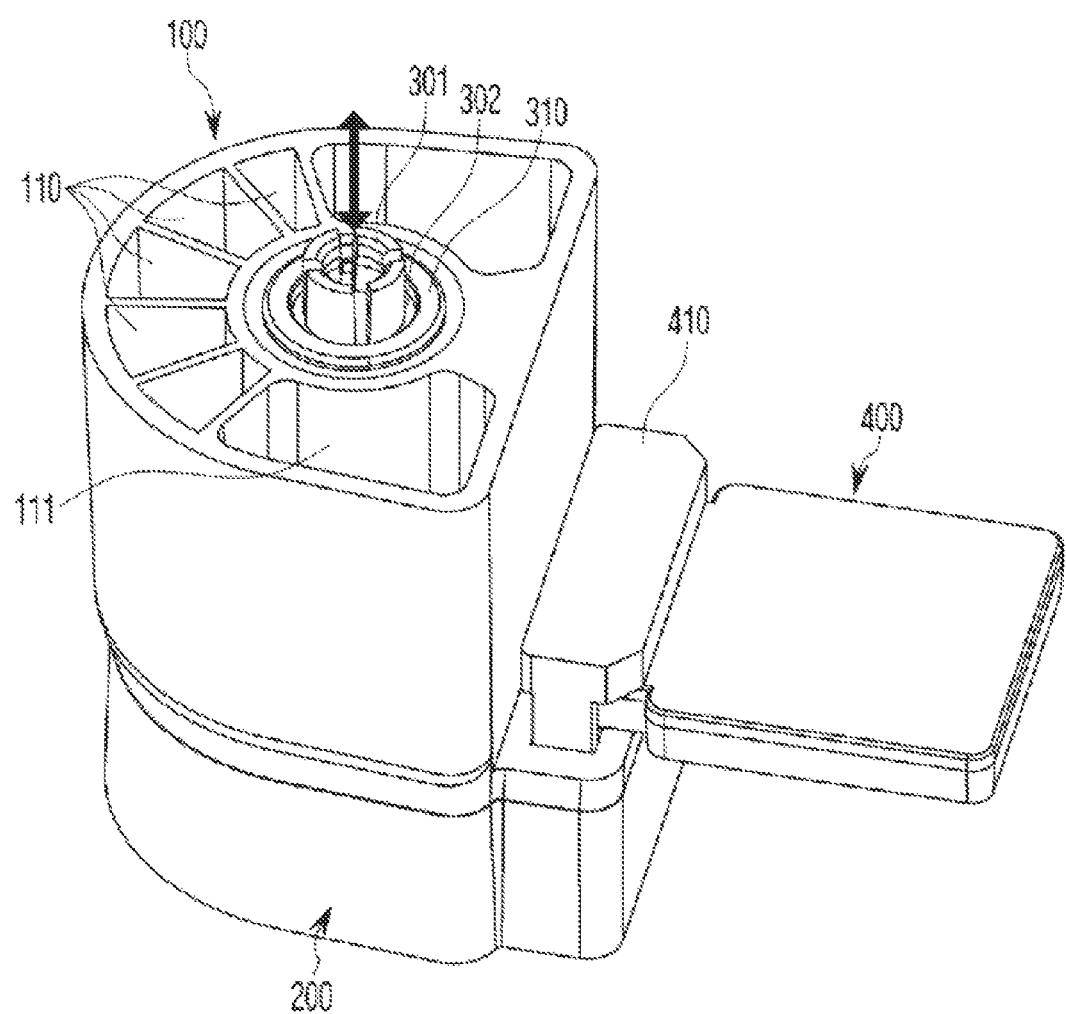
FIG. 2 is a perspective view of a cartridge for nucleic acid extraction apparatus according to an embodiment of the present invention.
Figure 3:
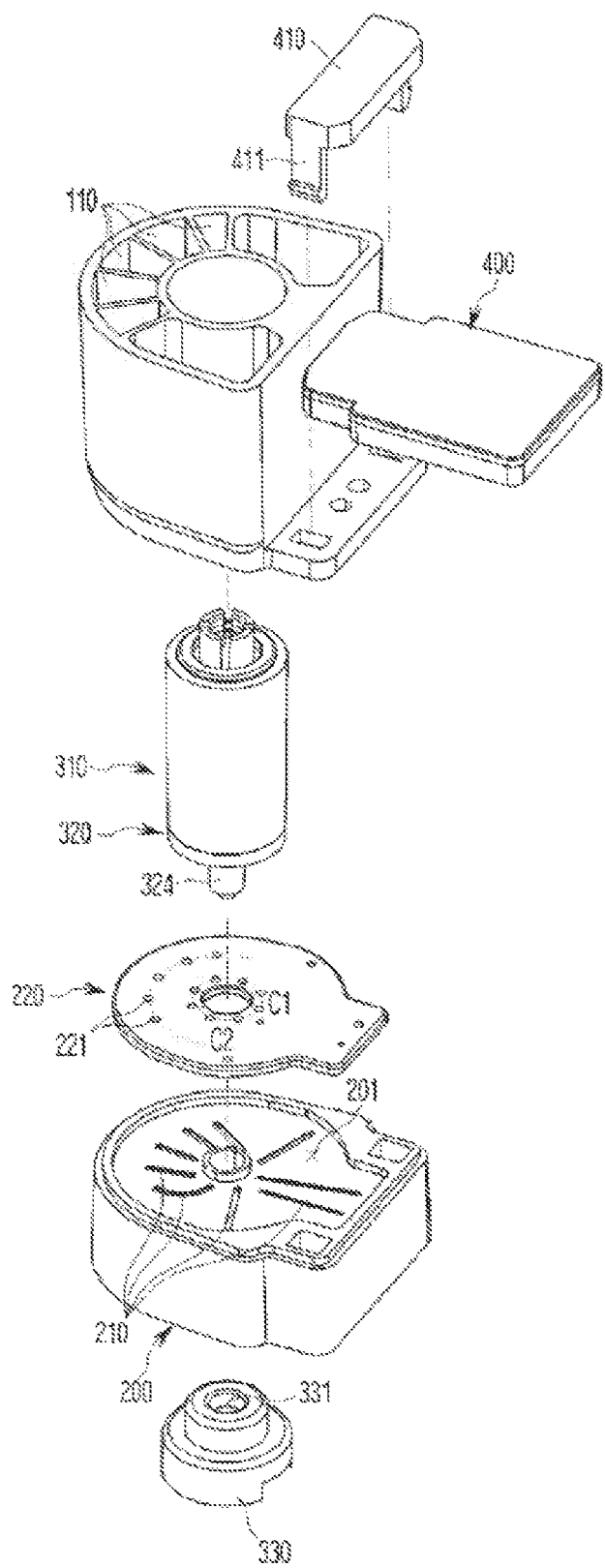
FIG. 3 is an exploded view of the cartridge for nucleic acid extraction apparatus according to an embodiment of the present invention.

FIG. 2 is a perspective view of the cartridge, and FIG. 3 is an exploded view of the cartridge shown in FIG. 2.

For reference with FIGS. 2 and 3, the cartridge for nucleic acid extraction can largely be included in a first body (100), a second body (200), a piston (300), a nucleic acid amplification module (400), and the like.

The first body (100) may be used for the purpose of storing a plurality of reagents.

According to the illustrated, the first body (100) may be formed of a plurality of chambers (110) forming a compartment separated from each other. Different reagents or samples are disposed in each chamber (110) and each chamber (110) forms an independent space so that the reagents do not mix with each other.

The second body (200) includes a path through which the reagent or sample stored in the first body (100) moves.

According to an embodiment of the present invention, the second body (200) may have a liquid flow path through which liquid can move and an air flow path through which air can move, and the second body (200) may include a pad (220) disposed on the upper surface to prevent leakage of liquid when combined with the first body (100). When the pad (220) and the second body (200) of cartridge are combined, the liquid flow path and the air flow path of the second body (200) are blocked by the pad (220) to form a space, thereby completing the perfect flow path (210).

The liquid flow path is connected to the first body (100) to provide a space for samples and reagents to move and mix.

The air flow path connects the amplification module and the vacuum control site of the piston (300) to control the vacuum that may occur when the extracted nucleic acid moves to the amplification module, and serves to prevent contamination of the nucleic acid amplification product.

A plurality of holes penetrating the pad (220) up and down may be formed in the pad (220). The liquid and air flow paths under the cartridge are connected to the plurality of reagent chambers (110) located in the first body (100) through the holes.

The center region of the pad (220) is coupled to be in close contact with the bottom surface of the piston lower body (320).

The holes formed in the center of the pad (220) overlap with the filter port or liquid port of the piston lower body (320) when the piston rotates.

More specifically, a plurality of flow paths (210) may be formed on the upper region of the second body (200). Each flow path (210) does not cross each other and is formed to extend from the center of the second body (200) to the outer region. As illustrated, some flow paths may have one end disposed on the same circumference and the other end also disposed on the same circumference with each other.

The pad (220) may be combined to the upper region of the second body (200).

A recessing region (201) recessed toward the bottom may be formed on the upper region of the second body (200), and the pad (220) may be engaged with the recessing region (201) on the upper region of the second body (200).

In other words, an outer wall surrounding the pad may be formed on the upper surface of the second body (200), and the outer wall may be formed to have the same height as the thickness of the pad.

The pad (220) may seal the flow paths (210) while being in close contact with the upper surface of the second body (200). The pad (220) may be formed of rubber or synthetic resin having elasticity so that the pad (220) may be more closely adhered to the second body (200).

According to an embodiment of the present invention, the holes are arranged to overlap the top and bottom of the ends of the flow paths (210). In other words, holes formed in the pad (220) may be paired in pairs to be connected through the flow path (210).

The pad (220) may include a plurality of holes disposed on the same circumference (C1) in the center and a plurality of holes disposed on the same circumference (C2) in the outer region.

The piston (300) may be comprised of a piston upper body (310) and a piston lower body (320).

In the upper body (310) of the piston (300), an inner space where reagents and samples can be mixed is formed, and a piston (300) control rod module moving up and down may be disposed in the inner space.

The piston control rod module may include a coupling region (301) coupled with a driving unit of the nucleic acid extraction device and a closed region (302) moving up and down in close contact with the piston inner space.

The piston lower body (320) is combined with the piston upper body (310) to form one body.

The piston lower body (320) may be combined with the rotation control module (330).

According to the illustrated, the piston upper body (310) is inserted into the hole formed in the central region of the first body (100) and the shaft (324) of the piston lower body (320) is inserted into the shaft hole (202) formed in the central region of the second body (200).

The shaft (324) of the piston lower body (320) is fixed in engagement with the rotation control module (330) combined to the bottom of the second body (200).

The nucleic acid amplification module (400) may be combined with the first body (100) or the second body (200).

An internal flow path may be formed inside the nucleic acid amplification module (400), and one end of the internal flow path may be formed to overlap with at least one of the flow paths (210) formed in the second body (200).

According to an embodiment of the present invention, there may be a fixing member (410) that covers the nucleic acid amplification module (400) and engages the first body (100) and the second body (200) so that the nucleic acid amplification module is not arbitrarily separated.

Fixing protrusions (411) fastened to the coupling grooves (102 and 203) formed in the first body (100) and the second body (200) may be formed at both ends of the fixing member (410).

Figure 4:
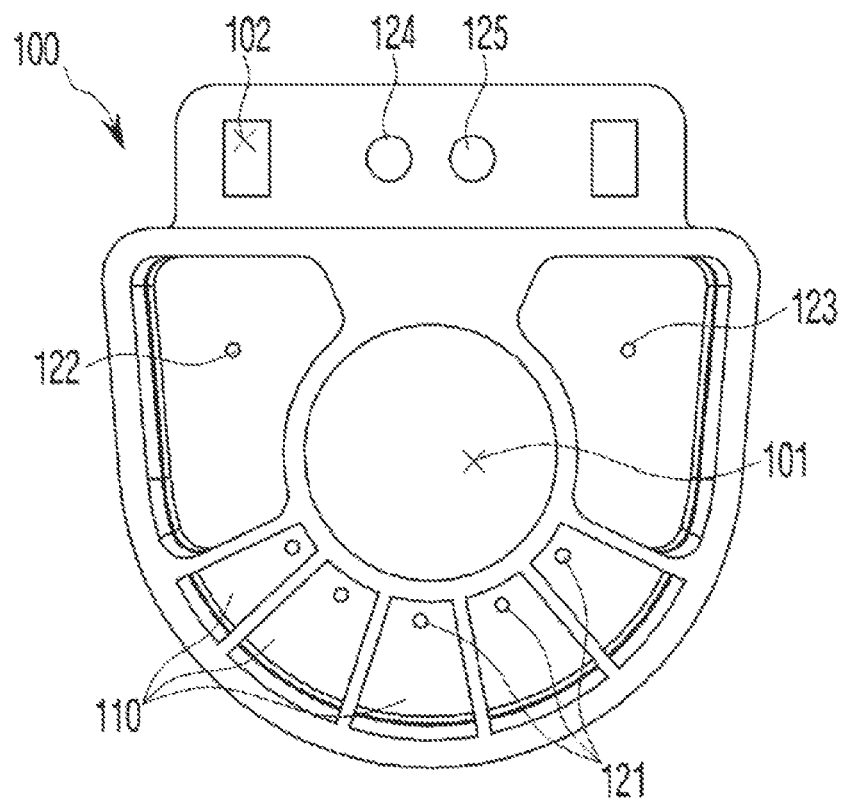
FIG. 4 is a plane view of the first body shown in FIG. 2.
Figure 5:
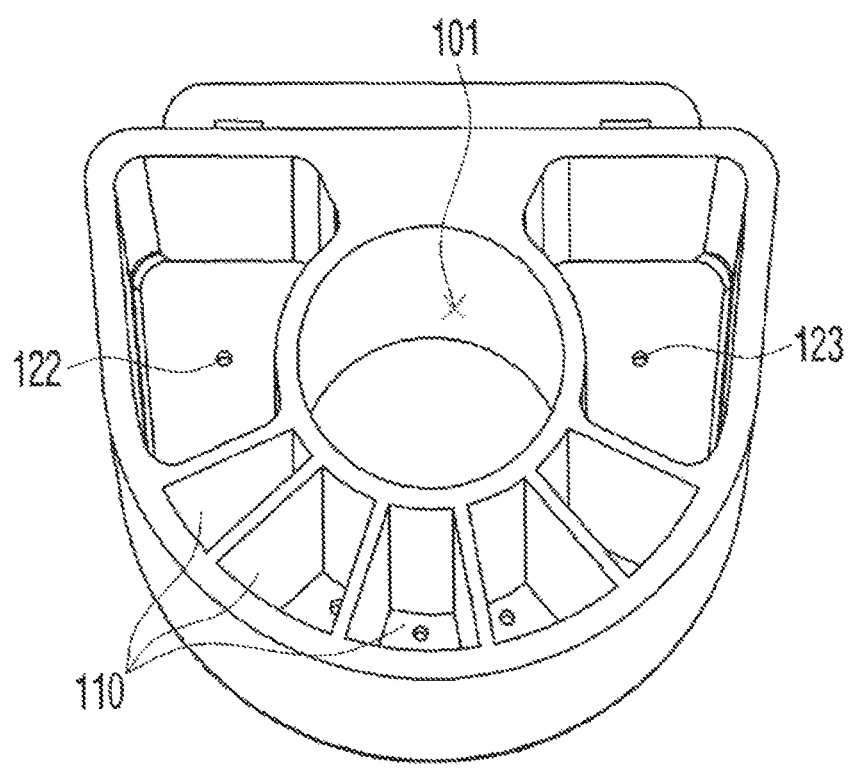
FIG. 5 is a conceptual view viewed by tilting the plane view of FIG. 4.
Figure 6:
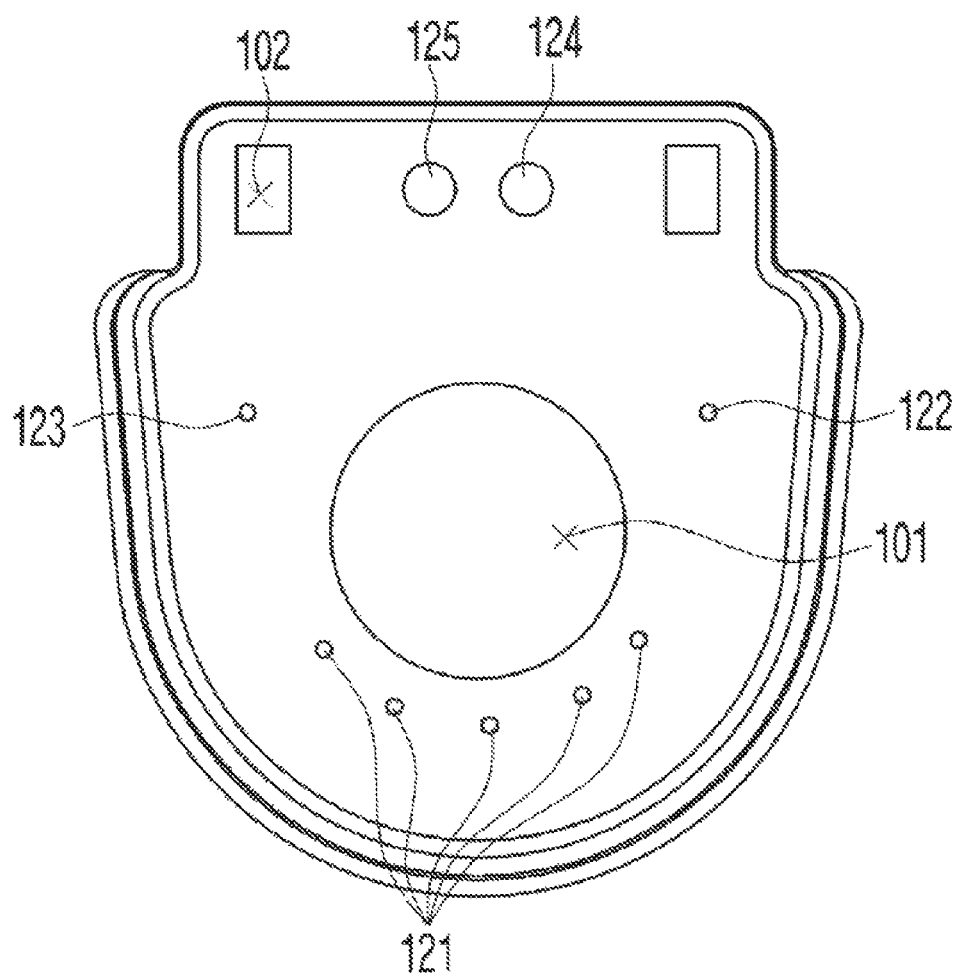
FIG. 6 is a bottom view of the first body shown in FIG. 2.
Figure 7:
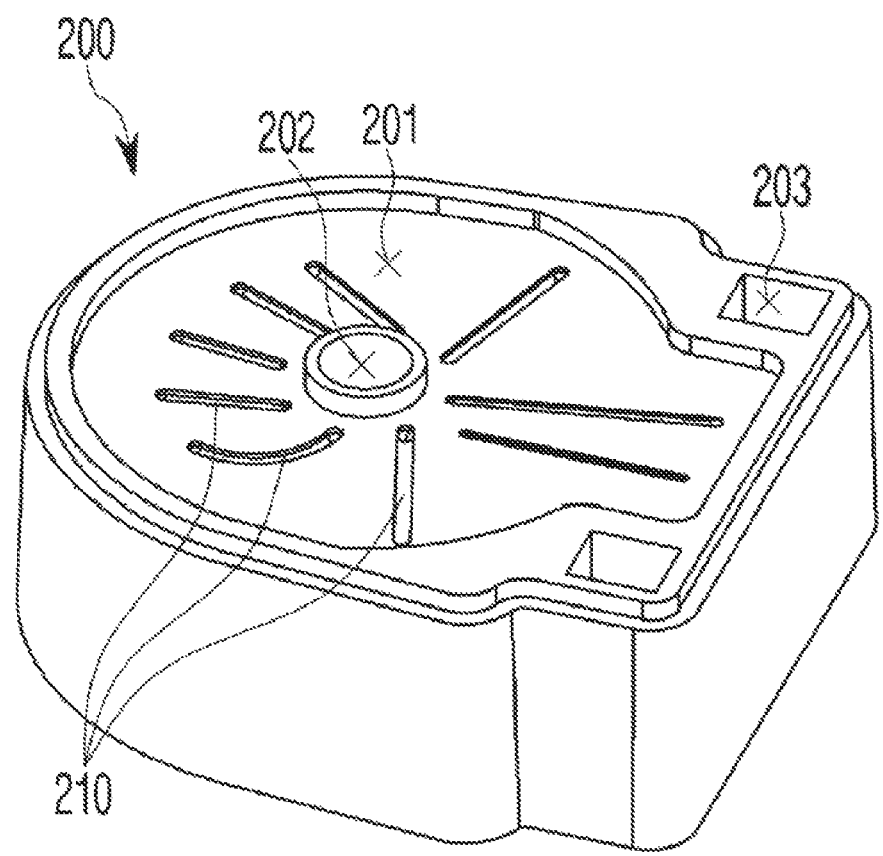
FIG. 7 is a perspective view of the second body shown in FIG. 2.

FIG. 4 is a plane view of the first body shown in FIG. 2, FIG. 5 is a conceptual view when the plan view of FIG. 4 is inclined, and FIG. 6 is a bottom view of the first body.

The structure of the first body (100) will be described in more detail with reference to FIGS. 4 to 6.

The first body (100) may include a plurality of reagent chambers (110), and each chamber (110) is formed to be isolated from each other.

At the bottom of each chamber (110), a port (121) overlapping holes formed in one end of the flow path (210) or the pad (220) is formed. Ports may have different distances from the center depending on the use of the chamber (110).

Each reagent chamber (110) includes a reagent chamber port. Each reagent chamber port is connected to the flow path of the second body (200) through the hole (221) of the rubber pad (220).

As shown, the sample chamber ports are disposed on the same circumference, and the master mix bead chamber port can be placed on a different circumference from the sample chamber port.

The sample chamber may include several dry beads required for sample extraction, and the master mix bead chamber may include several dry beads required for nucleic acid amplification.

The sample chamber and the master mix bead chamber are respectively connected to the sample chamber port and the master mix bead chamber port, and each port is connected to a hole formed in the pad and a flow path of the cartridge second body (200) to form a structure in which the liquid can move.

Figure 8:
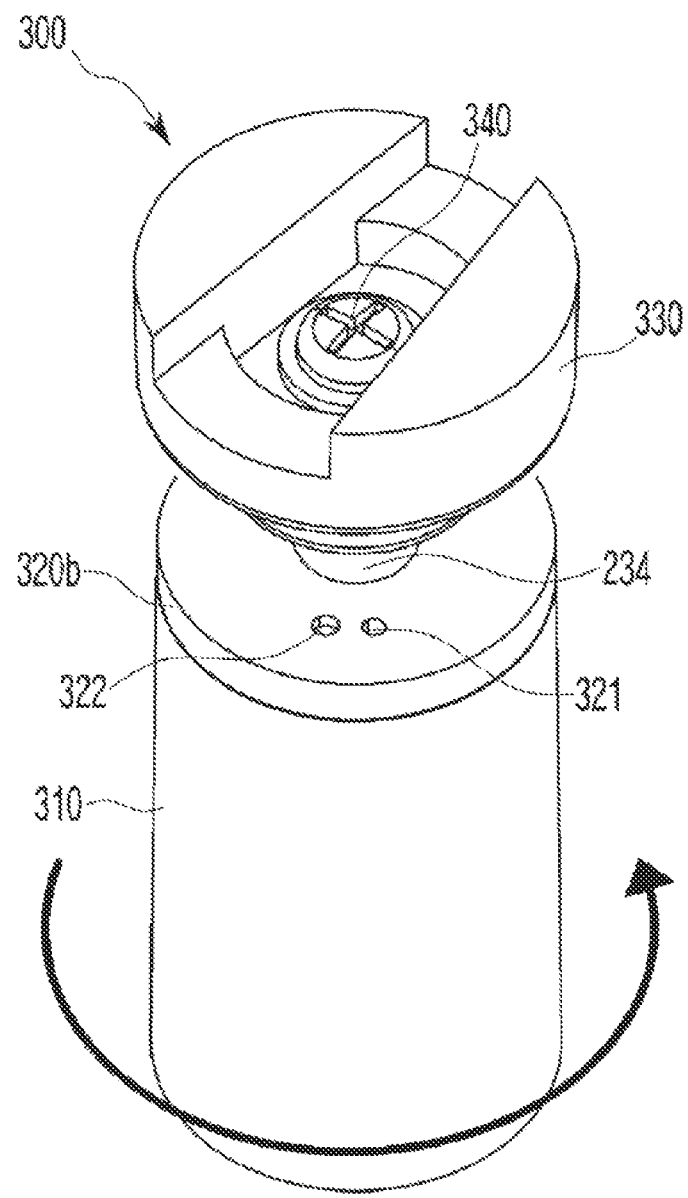
FIG. 8 is a bottom perspective view of a piston according to an embodiment of the present invention.
Figure 9:
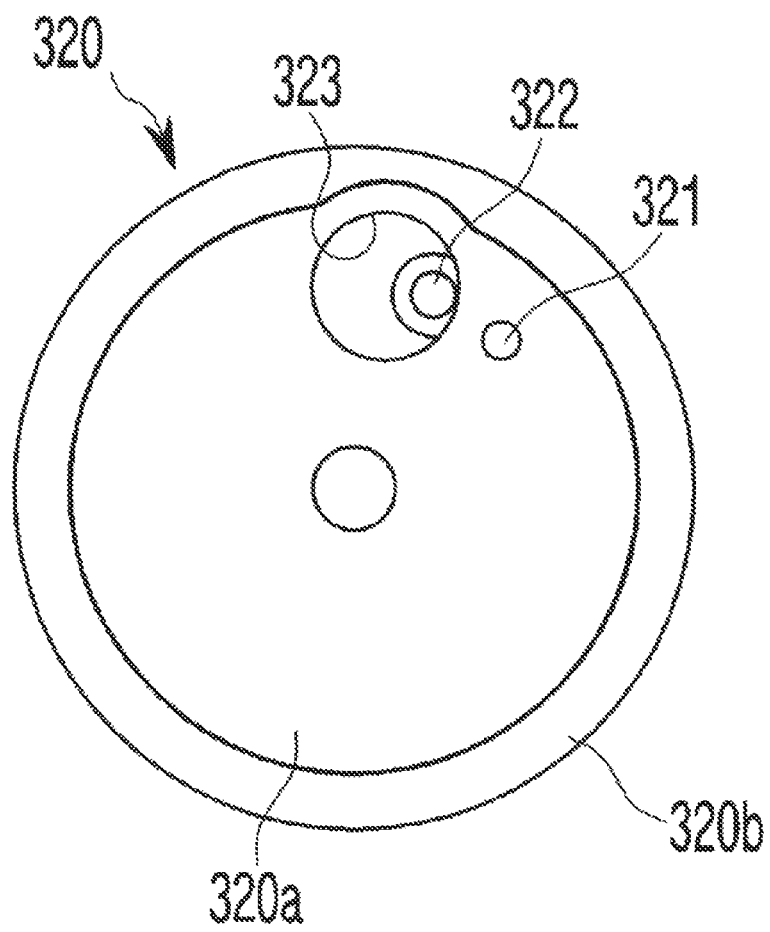
FIG. 9 is a plane view of the piston lower body.

FIG. 8 is a perspective view of a piston according to an embodiment of the present invention, FIG. 9 is a plane view of the piston lower body.

The piston shown in FIG. 8 is mounted on the cartridge described above to sequentially inhale and mix samples and reagents disposed in the cartridge chamber to extract nucleic acids.

According to the illustrated, the piston (300) may include an upper body (310), a lower body (320), a rotation control module (330), a control rod module, and the like.

The upper body (310) forms a cylindrical shape and may include a hollow.

A control rod module that moves up and down along the hollow may be disposed in the hollow of the upper body (310).

The control rod module may include a coupling region (301) coupled to the control rod of the nucleic acid extraction device, and an adhesion region (302) surrounding the outer circumference of the coupling region (301) and moving in close contact with the inner wall of the upper body (310).

At one end of the upper body (310), a coupling structure that engages with the lower body (320) may be formed, and a first hole connected to the liquid port of the lower body (320) and a second hole connected to the filter port of the lower body (320) may be formed. The second hole may be formed to have a smaller diameter than the filter recessed space of the filter port to prevent the support structure and the filter from coming off.

The lower body (320) may be coupled to one end of the upper body (310). More specifically, the lower body (320) is fixed in engagement with a coupling structure formed at one end of the upper body (310).

The lower body (320) may include a disk-shaped body, a shaft (324) formed to protrude from the center of the body to the outside, and a liquid port (321) and a filter port (322) disposed at the same distance from the center of the body. The body may be formed such that the central region (320a) protrudes compared to the outer region (320b). The central region (320a) can be fixed by being inserted into a groove formed on the coupling structure of the upper body.

The liquid port (321) is used to inhale, mix, and discharge samples and reagents into the piston, and the filter port (322) can be used to wash the nucleic acid capture filter or separate nucleic acids from the nucleic acid capture filter.

In addition, a groove recessed in the center direction may be formed on the outer periphery of the lower body (320). This groove may serve to remove the vacuum that may occur when moving liquid inside the cartridge.

The liquid port (321) and the filter port (322) are disposed at a certain angle from each other on the same circumference. For example, the filter port (322) and the liquid port (321) may be disposed apart from each other by 18 degrees to 36 degrees. More specifically, the two ports can be arranged to be spaced 22.5 degrees apart. In the case of using a step motor that divides into 16 circuits and performs one rotation, the positions of the liquid port (321) and the filter port (322) may be changed by one drive.

The filter port (322) of the lower body (320) may include a filter recessing space (323), and a filter and a support structure may be disposed in the filter recessing space. As a filter for capturing nucleic acids, a glass fiber filter having various particle sizes can be used, and the supporting structure serves to fix the filter for capturing nucleic acids.

The support structure may be formed of a porous plastic material having a certain particle size so as to prevent the separation of the filter and maintain a constant pressure when discharging the liquid.

The rotation control module (330) is connected to the driving unit of the equipment and serves as a medium for rotating the piston (300) at a certain angle.

The rotation control module (330) may include a coupling groove formed to engage the shaft at the center of one surface, and a driving groove formed to engage the drive shaft of the nucleic acid extraction device on the other surface.

The rotation control module (330) is coupled to the piston (300) to position the filter port and the liquid port to the appropriate reagent chamber port position so that various chemical reactions required in the nucleic acid extraction step can be performed inside one cartridge.

The liquid port and the filter port are separated by a certain angle, and the rotation control module (330) rotates the ports to a position suitable for each step when extracting nucleic acids.

After inserting the necessary filter for the collection of nucleic acids into the filter port, the lower body is combined with the upper body (310), and then combined to the first body (100) and the second body (200) to complete the cartridge setting.

The cartridge for nucleic acid extraction described above is not limited to the configuration and method of the above-described embodiments, but the above embodiments may be configured by selectively combining all or part of each embodiment so that various modifications can be made.

The inention claimed is:

1. A cartridge for nucleic acid extraction comprising:
   a first body having a plurality of chambers in which ports are formed at the bottom;
   a second body coupled to a lower region of the first body; and
   a piston disposed rotatably in the centers of the first body and the second body and having a port formed at the bottom thereof; wherein the cartridge comprises a plurality of flow paths formed on the upper region of the second body, one end overlapping the port of the piston and the other end overlapping the port of the first body.

2. The cartridge for nucleic acid extraction according to claim 1, wherein the port of the piston comprises at least two ports formed at a certain angle, and at least one of the ports is characterized in that a filter mounting region is formed.

3. The cartridge for nucleic acid extraction according to claim 2, wherein the two ports are characterized by being formed 22.5 degrees apart on the same circumference.

4. The cartridge for nucleic acid extraction according to claim 1, further comprising a pad disposed between the first body and the second body and covering the flow path.

5. The cartridge for nucleic acid extraction according to claim 4, wherein the pad comprises a plurality of holes overlapping the ends of the flow path.

6. The cartridge for nucleic acid extraction according to claim 5, wherein a recessing region to which the pad is combined is formed on an upper surface of the second body, and the pad is comprised of a rubber material and is formed to be fixed in engagement with the recessing region.

7. The cartridge for nucleic acid extraction according to claim 2, further comprising a nucleic acid amplification module mounted on the first body or the second body, one end having an internal flow path overlapping at least one of a plurality of flow paths.

8. The cartridge for nucleic acid extraction according to claim 7, wherein both ends of the internal flow path are respectively connected to the first flow path and the second flow path, when the first flow path overlaps the port of the piston, the second flow path is formed to overlap the vacuum removal groove of the piston.

9. The cartridge for nucleic acid extraction according to claim 8, wherein the vacuum removal groove and the port of the piston are disposed on different circumferences.

10. The cartridge for nucleic acid extraction according to claim 1, wherein the ports of the first body are formed on the same circumference.

* * * * *